United States Patent
Yoshida

(10) Patent No.: US 11,457,851 B2
(45) Date of Patent: Oct. 4, 2022

(54) SIGNAL PROCESSING APPARATUS, IMAGING APPARATUS, AND SIGNAL PROCESSING METHOD

(71) Applicant: CANON MEDICAL SYSTEMS CORPORATION, Otawara (JP)

(72) Inventor: Takami Yoshida, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1162 days.

(21) Appl. No.: 15/993,721

(22) Filed: May 31, 2018

(65) Prior Publication Data

US 2018/0344261 A1    Dec. 6, 2018

(30) Foreign Application Priority Data

Jun. 2, 2017    (JP) .............................. JP2017-110316

(51) Int. Cl.
| | |
|---|---|
| *A61B 5/349* | (2021.01) |
| *A61B 5/00* | (2006.01) |
| *A61B 5/352* | (2021.01) |
| *A61B 5/35* | (2021.01) |
| *A61B 5/055* | (2006.01) |

(52) U.S. Cl.
CPC ............... *A61B 5/349* (2021.01); *A61B 5/35* (2021.01); *A61B 5/352* (2021.01); *A61B 5/7285* (2013.01); *A61B 5/055* (2013.01)

(58) Field of Classification Search
None
See application file for complete search history.

(56) References Cited

U.S. PATENT DOCUMENTS

| | | | | | |
|---|---|---|---|---|---|
| 5,987,348 | A | * | 11/1999 | Fischer | G01R 33/5673 600/413 |
| 2010/0280402 | A1 | * | 11/2010 | Dunbar | A61B 5/0245 600/519 |
| 2014/0336522 | A1 | | 11/2014 | Nakata et al. | |
| 2016/0128643 | A1 | * | 5/2016 | Yoshida | A61B 5/352 600/413 |

OTHER PUBLICATIONS

Morphology-matching-based R-wave detection for noise-robust ECG gating by Yoshida et al. pub. Journal of Cardiovascular Magnetic Resonance 2016, 18(Suppl 1):P21 accessed online at <https://jcmr-online.biomedcentral.com/track/pdf/10.1186/1532-429X-18-S1-P21.pdf> (Year: 2016).*

Takami Yoshida et al., "Morphology-matching-based R-wave detection for noise-robust ECG gating", Journal of Cardiovascular Magnetic Resonance 2016, 18(Suppl 1):P21, 2 pages.

* cited by examiner

*Primary Examiner* — Katherine L Fernandez
*Assistant Examiner* — Michael S Kellogg
(74) *Attorney, Agent, or Firm* — Oblon, McClelland, Maier & Neustadt, L.L.P.

(57) ABSTRACT

In one embodiment, a signal processing apparatus that is configured to be connected to an imaging apparatus includes: a memory configured to store a predetermined program; and processing circuitry configured, by executing the predetermined program, to detect respective peaks of a plurality of biological signals related to heartbeat of plural leads, calculate difference in peak time between the plurality of biological signals, and detect a specific waveform included in the plurality of biological signals based on the difference in peak time.

7 Claims, 13 Drawing Sheets

SIGNAL PROCESSING APPARATUS, IMAGING APPARATUS, AND SIGNAL PROCESSING METHOD

CROSS-REFERENCE TO RELATED APPLICATION

This application is based upon and claims the benefit of priority from Japanese Patent Application No. 2017-110316, filed on Jun. 2, 2017, the entire contents of which are incorporated herein by reference.

FIELD

Embodiments described herein relate generally to a signal processing apparatus, an imaging apparatus, and a signal processing method.

BACKGROUND

An electrocardiograph is a device that attaches electrodes to a living body and measures potential difference between the electrodes. A signal measured by an electrocardiograph is called an electrocardiogram (ECG) signal and is widely used in the medical field. An ECG signal has, e.g., respective waveforms called a P-wave, an R-wave, a QRS complex, and a T-wave. Since these waveforms are used for diagnosis of various cardiac diseases and are also used for synchronization signals of a medical imaging apparatus capable of electrocardiographic (ECG) synchronization imaging, automatic detection of waveforms is important for industrial applications.

For instance, in image diagnosis of the heart with the use of a magnetic resonance imaging (MRI) apparatus, imaging may be performed at a timing synchronized with the systole or diastole of the heart by using a synchronization signal (also called a trigger signal) detected from each ECG signal. Such imaging is referred to as ECG synchronization imaging.

When ECG synchronization imaging is performed, a specific waveform in each ECG signal is detected to generate a trigger signal, and the start and end of imaging are controlled at a timing synchronized with the trigger signal. In particular, the trigger signal is often generated by detecting an R-wave in each ECG signal. In this case, imaging starts immediately after the R-wave in some cases, and it is desirable that the delay time from detection of the R-wave to generation of the trigger signal is as short as possible.

Since imaging with the use of an MRI apparatus involves application of a pulsed gradient magnetic field (hereinafter, referred to as a gradient pulse) and a pulsed radio-frequency magnetic field (hereinafter, referred to as an RF pulse), large noise that dynamically changes is superimposed on each ECG signal due to the application of these pulses. Even for the ECG signal on which such noise is superimposed, it is necessary to detect the synchronization signal with high reliability.

DETAILED DESCRIPTION

Hereinafter, respective embodiments of ECG-signal processing apparatuses, ECG synchronization imaging apparatuses, and ECG-signal processing methods will be described with reference to the accompanying drawings. In the embodiments described below, the same reference signs are given for identical components in terms of configuration and function, and duplicate description is omitted.

In one embodiment, a signal processing apparatus that is configured to be connected to an imaging apparatus includes: a memory configured to store a predetermined program; and processing circuitry configured, by executing the predetermined program, to detect respective peaks of a plurality of biological signals related to heartbeat of plural leads, calculate difference in peak time between the plurality of biological signals, and detect a specific waveform included in the plurality of biological signals based on the difference in peak time.

First Embodiment

Figure 1:
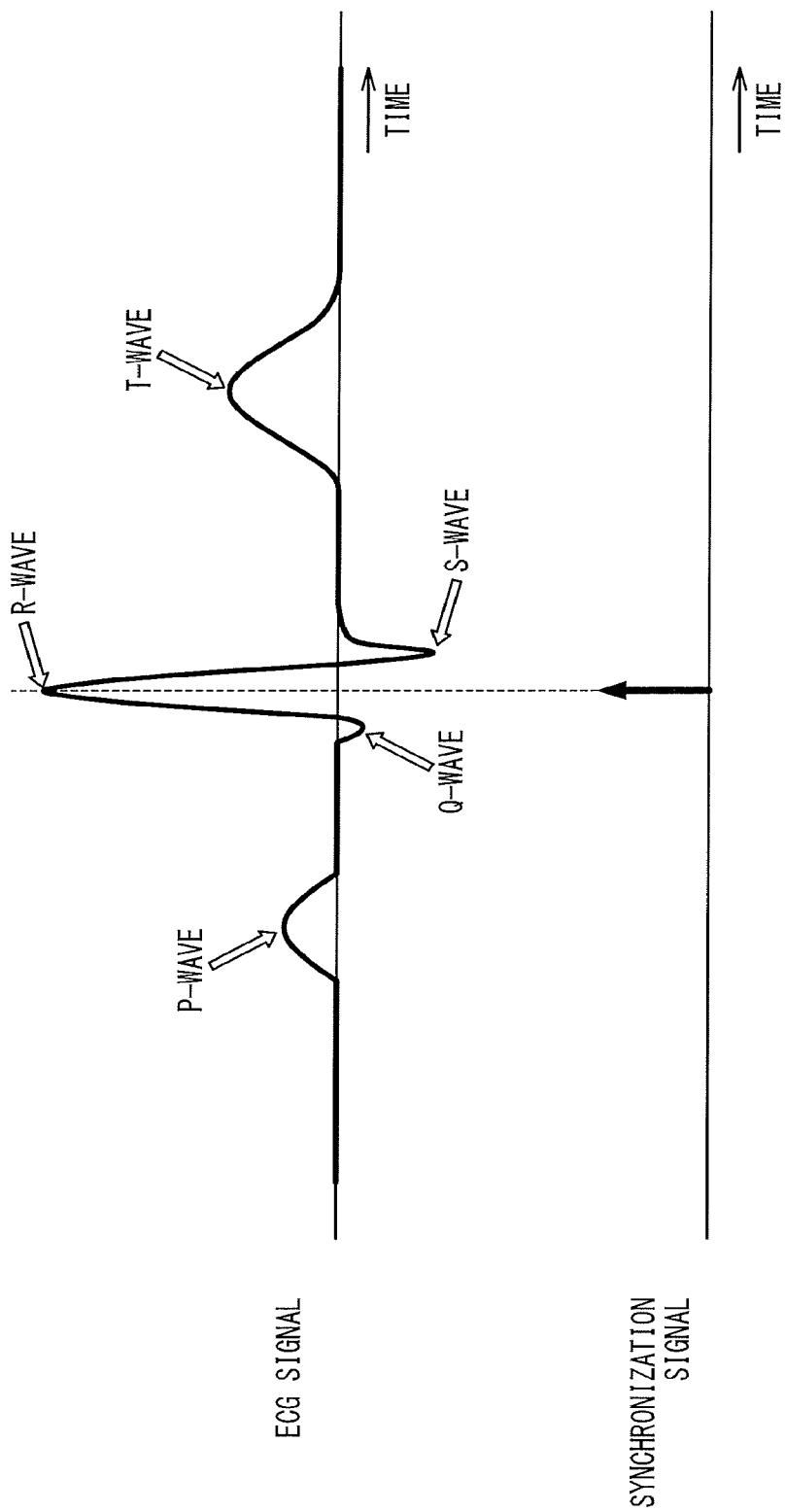
FIG. 1 is a schematic waveform diagram illustrating an ECG signal.

FIG. 1 is a schematic diagram illustrating an ECG signal to be detected by the ECG-signal processing apparatus 1 according to the first embodiment. As shown in FIG. 1, the ECG signal has specific waveforms such as a P-wave, an R-wave, an S-wave, and a T-wave.

Although a description will be given of an aspect of detecting R-waves among specific waveforms in each of the following embodiments, this is only one aspect and embodiments of the present invention are not limited to such an aspect. The ECG-signal processing apparatus 1 of each embodiment can perform ECG synchronization imaging by detecting waveforms other than R waves (e.g., P-waves, S-waves, and T-waves).

As shown in FIG. 1, the ECG-signal processing apparatus 1 of the first embodiment detects a heartbeat synchronization signal (hereinafter, simply referred to as a synchronization signal) from each R-wave, and provides the synchronization signal to an apparatus that performs ECG synchronization imaging. As an ECG synchronization imaging apparatus (imaging apparatus) 300 that can perform imaging in synchronization with heartbeat, e.g., a CT (Computed Tomography) apparatus and an MRI (Magnetic Resonance Imaging) apparatus are available. For instance, the ECG synchronization imaging apparatus 300 uses an imaging method (ECG synchronization imaging method) in which a start timing of data acquisition is determined on the basis of a position of the R-wave. The ECG synchronization imaging apparatus 300 inputs a synchronization signal corresponding to the position of the R-wave, and determines the start timing of data acquisition on the basis of the input synchronization signal. Although depending on the purpose of imaging, image data need to be acquired immediately after the R-wave. Thus, it is necessary to shorten the delay time, i.e., time from detecting the R-wave in each ECG signal to generating the synchronization signal.

For instance, in the case of an MRI apparatus, various types of non-contrast enhanced MRA (Magnetic Resonance Angiography) methods are used, such as an FBI (Fresh Blood Imaging) method or a Time-SLIP (Time-Spatial Labeling Inversion Pulse) method. In data acquisition under the FBI method, for instance, the MRI apparatus acquires a diastolic image and a systolic image by controlling the timing of data acquisition with reference to the synchronization signal, and calculates a difference image between the diastolic image and the systolic image so as to obtain a blood vessel image in which an artery is depicted. On the other hand, in data acquisition under the Time-SLIP method, the MRI apparatus can obtain a blood flow image by, e.g., controlling a timing of applying each labeling pulse and a timing of data acquisition with reference to the synchronization signal. In this way, the MRI apparatus controls each timing of data acquisition and respective application timings of various pulses with reference to the synchronization signal generated from the ECG signal. Since these timings are often immediately after the R-wave, it is desirable that the delay time is as short as possible. Note that above-described imaging methods are merely some possible examples, and the MRI apparatus performs imaging by using the synchronization signal as a reference in other imaging methods such as contrast enhanced imaging or various imaging methods that targets the heart.

The waveform of the ECG signal exemplified in FIG. 1 is not influenced by noise or other unnecessary waveforms, and has a waveform in which the R-wave appears conspicuously. However, for instance, in the ECG signal observed while an object is inside the bore of the MRI apparatus, there is influence of blood flowing in a static magnetic field and thus it is not necessarily the case that only the R-wave appears as a conspicuous waveform. Additionally, in an imaging period during which the MRI apparatus performs a pulse sequence, large noise is superimposed on the ECG signal due to influence of gradient pulses and RF pulses applied during the imaging period.

Thus, in the ECG-signal processing apparatus 1 of the present embodiment, in order to reduce erroneous detection due to noise and improve detection accuracy of the R-wave, the R-wave is detected by using biological signals related to heartbeat of plural leads.

Although, in the following, a description will be given for a case where two signals of a lead I and a lead II out of plural ECG signals outputted from an electrocardiograph, embodiments of the present invention are not limited to the case of using the leads I and II.

For instance, in the case of a 12-lead electrocardiograph, respective signals of a lead III, a lead aVR, a lead aVL, a lead aVF, and leads V1 to V6 are outputted in addition to the leads I and II. These signals of plural leads can also be used for detecting the R-wave. Further, a pulse wave signal, a heart sound signal, and a vector cardiogram may be used for detecting the R-wave.

The ECG signals of plural leads are plural signals simultaneously observing an electric signal propagating through the heart from plural positions. For instance, among electrodes of a 12-lead electrocardiograph, respective four electrodes used for four limb leads are attached to the right hand, the left hand, the right foot, and the left foot. In this case, the lead I is voltage difference from the right-hand direction as viewed from the left-hand direction. In other words, the lead I is the potential difference between the right-hand electrode and the left-hand electrode. Similarly, the lead II is voltage difference from the right-hand direction as viewed from the direction of the left foot. In other words, the lead II is the potential difference between the electrode on the left foot and the electrode on the right hand.

Figure 2:
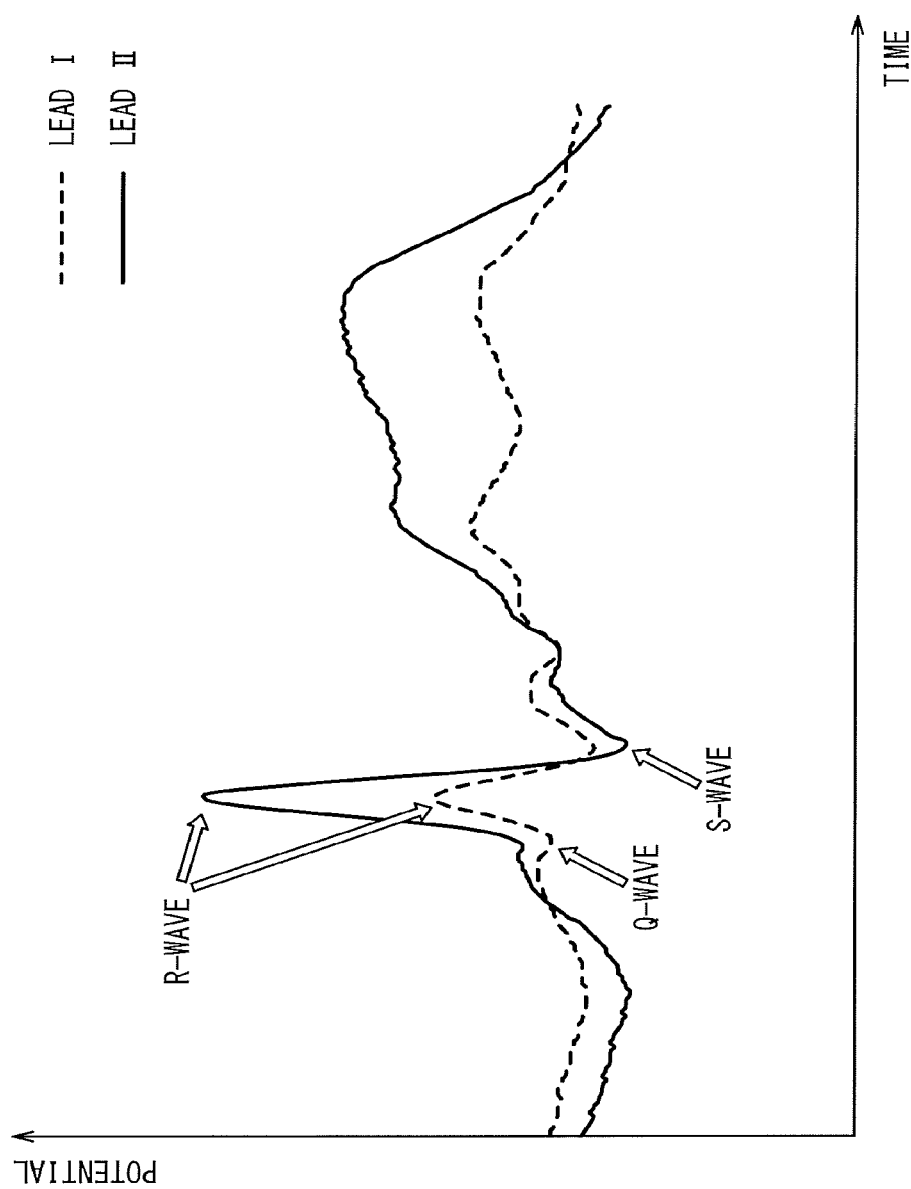
FIG. 2 is a diagram illustrating a lead I and a lead II of an ECG signal.

FIG. 2 is a schematic diagram illustrating waveforms of the respective ECG signals of the lead I and the lead II. As described above, the ECG signals of plural leads are signals observed from different positions. Thus, even for one R-wave, its shape changes, e.g., between the lead I and the lead II as shown in FIG. 2. By using this change as a clue to discriminate between the R-wave and other waveforms, erroneous detection of the R-wave is reduced to improve the accuracy of detecting the R-wave in the present embodiment.

Figure 3:
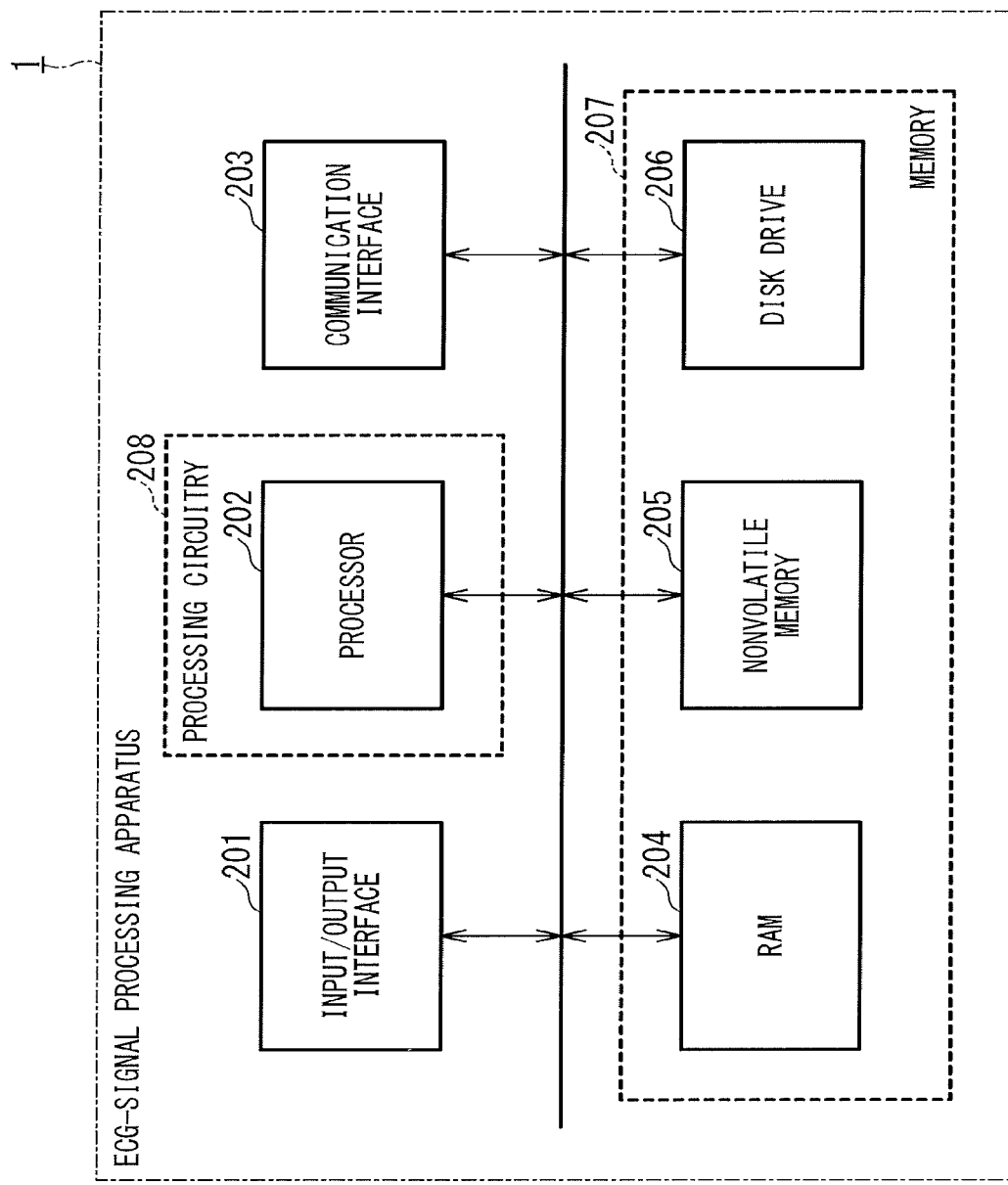
FIG. 3 is a diagram illustrating a hardware configuration of an ECG-signal processing apparatus.

FIG. 3 is a block diagram illustrating an example of the hardware configuration of the ECG-signal processing apparatus 1. The ECG-signal processing apparatus 1 includes an input/output interface 201, processing circuitry 208, a communication interface 203, and a memory 207. Further, the memory 207 includes a random access memory (RAM) 204, a nonvolatile memory 205, and a disk drive 206.

The nonvolatile memory 205 of the memory 207 is, e.g., a storage device such as a hard disk and a flash memory, and stores various programs and data.

The processing circuitry 208 is configured as, e.g., one or plural processor(s) 202. The term "processor" includes a special-purpose or general-purpose processor such as a central processing unit (CPU) or a signal processing processor. The processor 202 of the processing circuitry 208 implements various functions of the ECG-signal processing apparatus 1 described below by software processing, i.e., processing of reading out one or more programs from the nonvolatile memory 205 to the RAM 204 and executing them. The processor 202 may read out programs stored in a recording medium such as a magnetic disk, an optical disk, or a USB memory, from the disk drive 206 or the input/output interface 201, in addition to the programs stored in the nonvolatile memory 205. In addition, the processor 202 may download programs from an external server via the communication interface 203.

The processing circuitry 208 may be configured as hardware such as an application specific integration circuit (ASIC) or a field-programmable gate array (FPGA). The various functions of the ECG-signal processing apparatus 1 can also be implemented by hardware processing to be executed by an ASIC, an FPGA, or a special-purpose electronic circuit. Moreover, the processing circuitry 208 may implement the various functions of the ECG-signal processing apparatus 1 by combining hardware processing and software processing.

Figure 4:
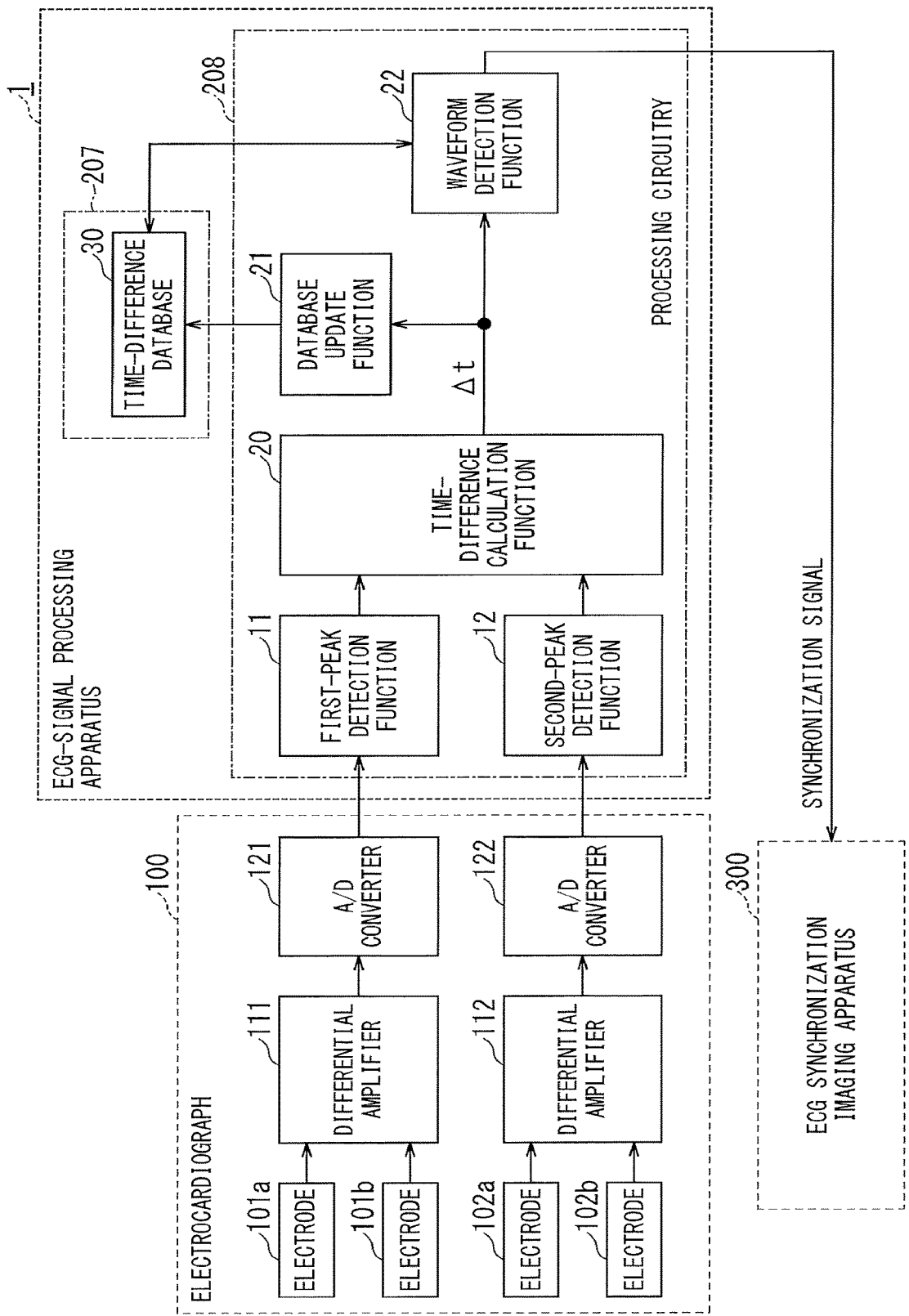
FIG. 4 is a block diagram illustrating a configuration of the ECG-signal processing apparatus according to the first embodiment.

FIG. 4 is a block diagram illustrating a functional configuration of the ECG-signal processing apparatus 1 of the first embodiment and configurations of respective apparatuses connected to the ECG-signal processing apparatus 1. An electrocardiograph 100 generates two ECG signals including the lead I and the lead II as examples of ECG signals of plural leads, and transmits them to the ECG-signal processing apparatus 1. The ECG-signal processing apparatus 1 generates a synchronization signal from the received ECG signals and transmits the synchronization signal to the ECG synchronization imaging apparatus 300. The ECG synchronization imaging apparatus 300 performs imaging of an object on the basis of the synchronization signal.

The electrocardiograph 100 includes electrodes 101a, 101b, 102a, and 102b, differential amplifiers 111 and 112, and A/D converters 121 and 122. The electrodes 101a, 101b, 102a, and 102b are attached to the surface of the object.

The differential amplifier 111 amplifies a weak potential difference between the electrodes 101a and 101b, and the differential amplifier 112 amplifies a weak potential difference between the electrodes 102a and 102b. The A/D converter 121 converts the analog signal amplified by the differential amplifier 111 into a digital signal, and the A/D converter 122 converts the analog signal amplified by the differential amplifier 112 into a digital signal.

For instance, the electrodes 101a and 101b are respectively attached to the left hand and the right hand, and the differential amplifier 111 and the A/D converter 121 output the ECG signal corresponding to the lead I.

Meanwhile, the electrodes 102a and 102b are respectively attached to the left foot and the right hand, and the differential amplifier 112 and the A/D converter 122 output the ECG signal corresponding to the lead II.

Although the electrocardiograph 100 shown in FIG. 4 exemplifies four electrodes 101a, 101b, 102a, and 102b, the number of electrodes is not limited to four as described above. For instance, in order to obtain a 12-lead electrocardiogram, the electrocardiograph may be configured to include four electrodes attached to the respective four limbs and six electrodes attached to the chest. Additionally, instead of the method of obtaining the potential difference between two electrode attachment points of the body, a method of recording the potential difference between a predetermined reference point and an electrode attachment point may be used. Although the electrocardiograph 100 equipped with two differential amplifiers 111 and 112 and two A/D converters 121 and 122 is exemplified, number of the differential amplifiers and number of the A/D converters are not limited to two.

As described above, the ECG-signal processing apparatus 1 includes at least the processing circuitry 208 and the memory 207. The memory 207 stores a time-difference database 30. Details of the time-difference database 30 will be described below.

The processing circuitry 208 implements a first-peak detection function 11, a second-peak detection function 12, a time-difference calculation function 20, a database update function 21, and a waveform detection function 22 by causing the processor 202 of the processing circuitry 208 to execute the programs read out from the memory 207.

The first-peak detection function 11 acquires the first ECG signal from the electrocardiograph 100 via the input/output interface 201. The first ECG signal is, e.g., an ECG signal corresponding to the lead I. Further, the first-peak detection function 11 performs filter processing on the acquired first ECG signal in order to enhance an R-wave component and suppress a noise component. In this filtering process, a low pass filter, a high pass filter, a band pass filter, or a combination of these filters is used. In the following, a description will be given of a case where the R-wave component is enhanced by the filter processing. The first ECG signal in which the R-wave component is enhanced is referred to as a first enhanced ECG signal.

Further, the first-peak detection function 11 compares the value of the first enhanced ECG signal with a predetermined first threshold value. When the value of the first enhanced ECG signal exceeds the first threshold value as a result of the comparison, the first-peak detection function 11 determines that the first peak is detected, and then outputs the time corresponding to the first peak as the first peak time to the time-difference calculation function 20.

In the meantime, the second-peak detection function 12 acquires the second ECG signal from the electrocardiograph 100 via the input/output interface 201. The second ECG signal is, e.g., an ECG signal corresponding to the lead II. The second-peak detection function 12 generates the second enhanced ECG signal by performing filter processing on the acquired second ECG signal in a manner similar to the first-peak detection function 11. Further, the second-peak detection function 12 compares the value of the second enhanced ECG signal with a predetermined second threshold value. When the value of the second enhanced ECG signal exceeds the second threshold value as a result of the comparison, the second-peak detection function 12 determines that the second peak is detected, and then outputs the time corresponding to the second peak as the second peak time to the time-difference calculation function 20, similarly to the first-peak detection function 11.

The first-peak detection function 11 and the second-peak detection function 12 may output the absolute value of the first enhanced ECG signal and the absolute value of the second enhanced ECG signal, respectively, in order to deal with the case where the R-wave appears on the minus side in the filtering processing for enhancing the R-wave. For instance, when arrhythmia occurs or when the attachment positions of the electrodes 101 and 102 are not appropriate with respect to the position or orientation of the heart, the R-wave sometimes appears on the minus side. In such a case, the detection of the R-wave appearing on the minus side is missed unless an absolute value is used. In the following description, it is assumed that the first and second enhanced ECG signals are calculated as absolute values after the filtering processing.

The time-difference calculation function 20 calculates difference Δt between the first peak time detected by the first-peak detection function 11 and the second peak time detected by the second-peak detection function 12. In general, even when the peak is detected for each of the ECG signals of plural leads acquired from the same object, the peak times separately detected for the ECG signals of the respective leads do not necessarily coincide with each other. Thus, the time-difference calculation function 20 calculates how much difference exists in peak time between leads.

The database update function 21 updates the time-difference database 30 in which peak time differences calculated by the time-difference calculation function 20 are summed up, each time the peak time difference is calculated. As a summing up method of the peak time differences, the occurrence frequency may be summed up by counting up the occurrence frequency for each time difference, or the occurrence frequency may be calculated as the occurrence probability normalized by the total number of the detected peaks. Further, when summing up the peak time differences, only peak time differences smaller than a specific threshold value may be summed up.

The waveform detection function 22 compares the time differences calculated by the time-difference calculation function 20 with the occurrence frequency (or occurrence probability) of each time difference stored in the time-difference database 30 so as to determine whether the detected peak is indicative of the R-wave or caused by other factors such as noise.

Note that, in the case of a peak caused by the R-wave, a peak is normally detected once per heartbeat. Thus, when the ECG signals are monitored for a long time, the number of occurrences of the peak time difference corresponding to the R-wave increases with time.

By contrast, in the case of a peak caused by noise, its occurrence frequency is lower than that of heartbeat and its peak time difference between plural leads is not necessarily constant. Thus, the occurrence frequency of the peak time difference calculated when noise is detected as a peak is not so high.

Figure 5:
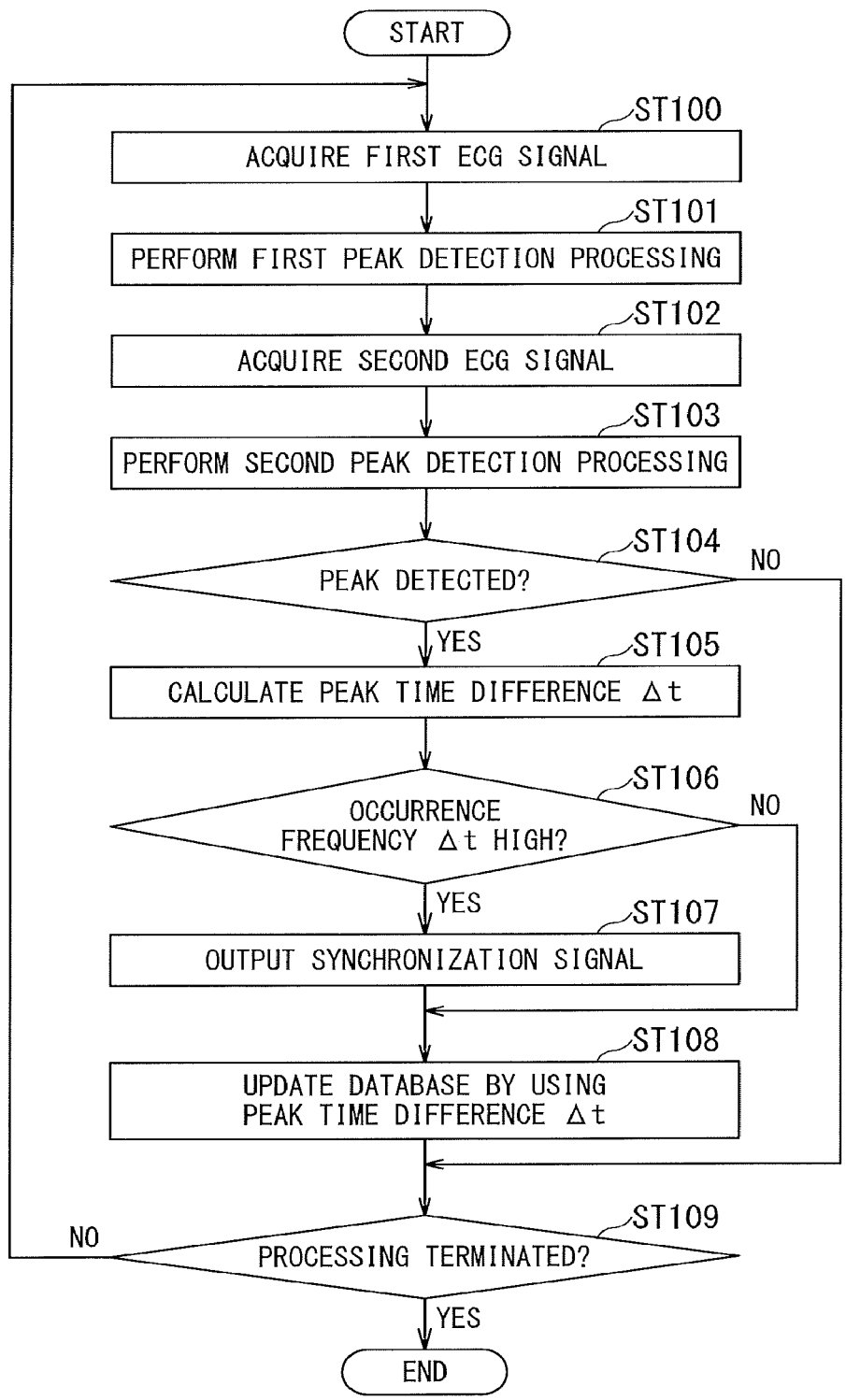
FIG. 5 is a flowchart illustrating processing performed by the ECG-signal processing apparatus according to the first embodiment.

FIG. 5 is a flowchart illustrating an outline of processing performed by the ECG-signal processing apparatus 1 according to the first embodiment. FIG. 6 to FIG. 9 are diagrams illustrating the processing concept of the ECG-signal processing apparatus 1. Hereinafter, the processing performed by the ECG-signal processing apparatus 1 will be described on the basis of the step number of FIG. 5 by referring to FIG. 6 to FIG. 9 as required.

The steps ST100 and ST101 are steps corresponding to the first-peak detection function 11 of the processing circuitry 208.

In the step ST100, the processing circuitry 208 acquires the first ECG signal corresponding to the lead I as a time-sequential signal from the electrocardiograph 100, for instance. The ECG signal inputted to the processing circuitry 208 is, e.g., a digital signal sampled at 1000 Hz (i.e., sampled at a sampling interval of 1 ms) in the A/D converter 121 of the electrocardiograph 100.

In the next step ST101, the processing circuitry 208 generates the first enhanced ECG signal by performing the filtering processing on the first ECG signal. Then, the processing circuitry 208 determines whether a peak is detected or not, by comparing the first enhanced ECG signal with the first threshold value.

The steps ST102 and ST103 are steps corresponding to the second-peak detection function 12 of the processing circuitry 208.

In the step ST102, the processing circuitry 208 acquires the second ECG signal corresponding to the lead II as a time-sequential signal from the electrocardiograph 100, for instance. The ECG signal inputted to the processing circuitry 208 is a digital signal sampled in the A/D converter 122 of the electrocardiograph 100 in synchronization with the first ECG signal.

In the next step ST 103, the processing circuitry 208 generates the second enhanced ECG signal by performing the filtering processing on the second ECG signal. Then, the processing circuitry 208 determines whether a peak is detected or not, by comparing the second enhanced ECG signal with the second threshold value.

The first threshold value and the second threshold value may be respectively determined from the first enhanced ECG signal and the second enhanced ECG signal. Alternatively, the first threshold value and the second threshold value may be fixed values determined in advance.

In the next step ST104, the processing circuitry 208 determines whether a peak is detected in the first-peak detection function 11 and the second-peak detection function 12 or not. When a peak is detected at least one of the first-peak detection function 11 and the second-peak detection function 12 (YES in the step ST104), the processing proceeds to the step ST105. On the other hand, when neither the first-peak detection function 11 nor the second-peak detection function 12 detects a peak (NO in the step ST104), the processing proceeds to the step ST109.

In the step ST105, the processing circuitry 208 acquires the latest peak time detected by the first-peak detection function 11 and the latest peak time detected by the second-peak detection function 12, and calculates the peak time difference $\Delta t$ between both.

Figure 6:
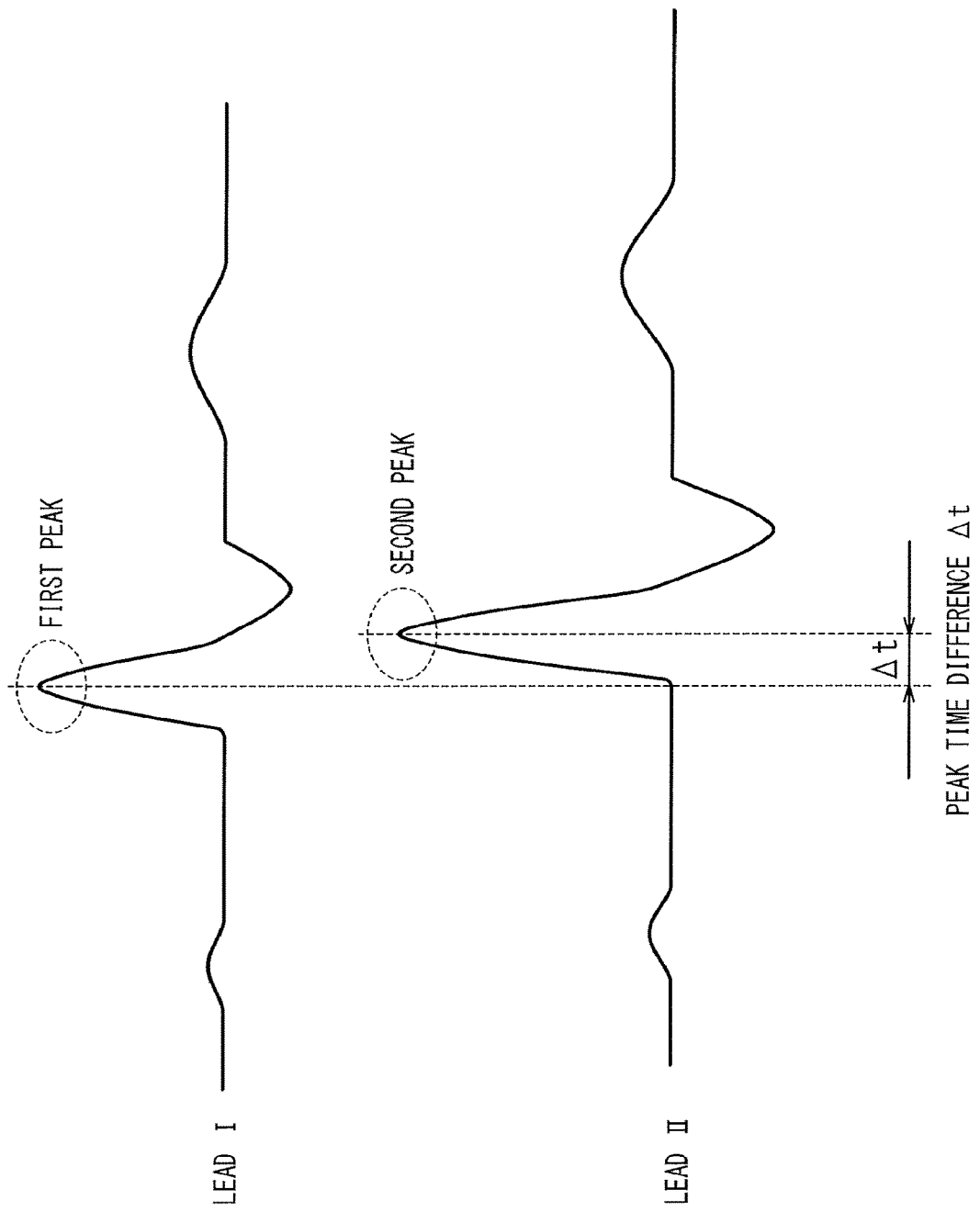
FIG. 6 is a schematic diagram illustrating a processing concept of calculating peak time difference.

FIG. 6 is a schematic diagram illustrating the concept of the processing from the steps ST100 to ST105. As shown in FIG. 6, for instance, the peak time difference $\Delta t$ is calculated as the difference between the time of the first peak detected in the ECG signal of the lead I and the time of the second peak detected in the ECG signal of the lead II in the step ST105.

In the step ST106, the processing circuitry 208 determines whether the occurrence frequency of the calculated peak time difference $\Delta t$ is high or not, by referring to the time-difference database 30. In the time-difference database 30, the history of the peak time differences calculated from the peaks detected in the past is stored in such a manner that the respective peak time differences are associated with the occurrence frequency of the peak time differences.

Figure 7:
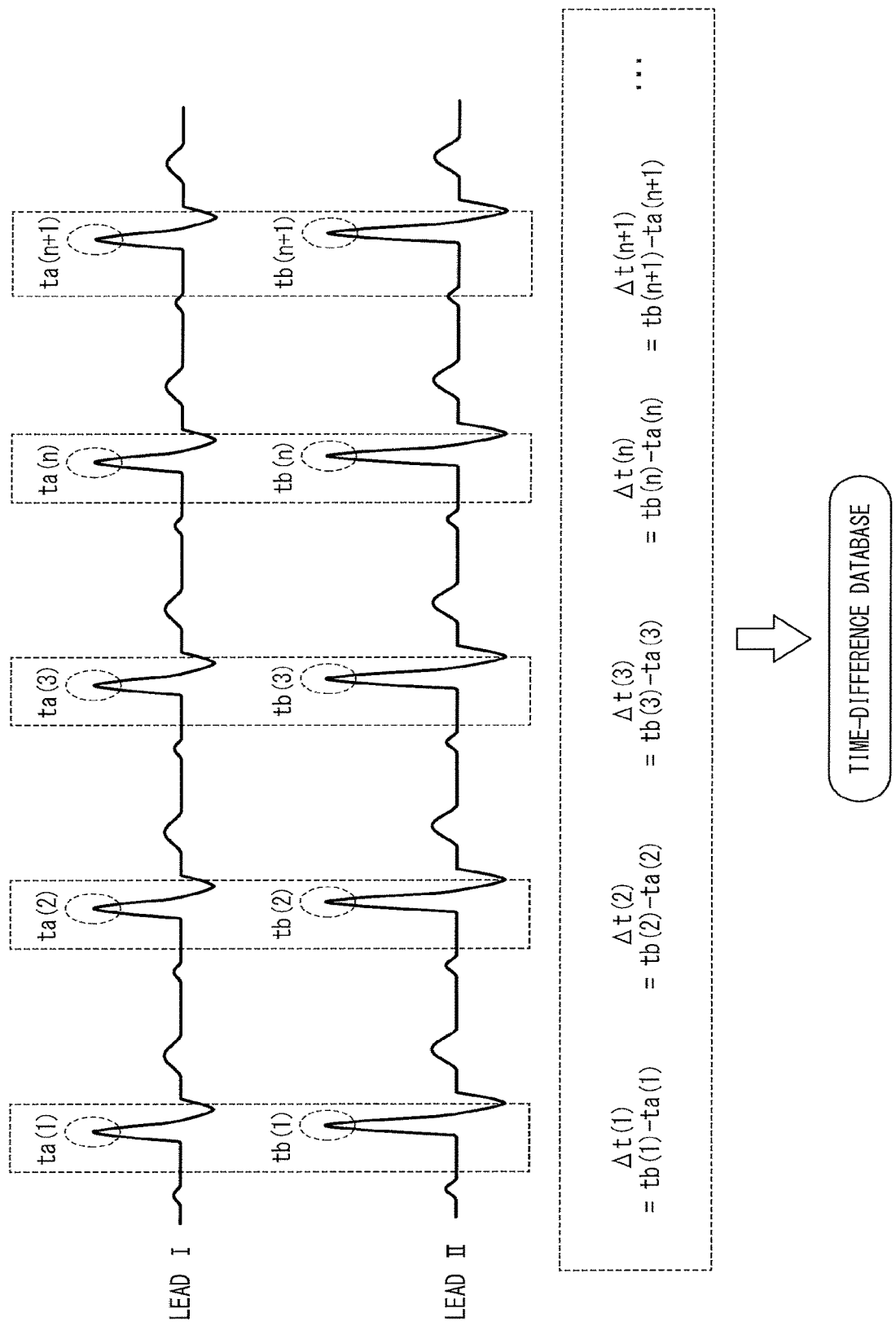
FIG. 7 is the first diagram illustrating a concept of generating and updating a time-difference database.

FIG. 7 is a schematic diagram illustrating the concept of the procedure of generating or updating the time-difference database 30 to be performed by the database update function 21. As shown in the upper part of FIG. 7, the first-peak detection function 11 detects the first peak from the ECG signal corresponding to the lead I and calculates the respective detection times $ta(1), ta(2), ta(3), \ldots, ta(n)$, and $ta(n+1)$. Similarly, the second-peak detection function 12 detects the second peak from the ECG signal corresponding to the lead II and calculates the respective detection times $tb(1), tb(2), tb(3), \ldots, tb(n)$, and $tb(n+1)$ as shown in the middle part of FIG. 7. Further, the time-difference calculation function 20 sequentially calculates respective time differences between the first peak and the second peak as $\Delta t(1), \Delta t(2), \Delta t(3), \ldots, \Delta t(n)$, and $\Delta t(n+1)$.

The database update function 21 classifies each time difference into a classification (i.e., section or division) of a predetermined time width, and counts the occurrence frequency of the time difference for each classification. The database update function 21 constructs the time-difference database 30 by classifying the time difference $\Delta t$ into classifications of 2 ms width, for example, and sequentially counting the number of occurrence of the time difference $\Delta t$ falling into each classification. For instance, each time difference $\Delta t$ satisfying $0 \leq \Delta t < 2$ ms is classified into the classification "0 ms", each time difference $\Delta t$ satisfying $2 \leq \Delta t < 4$ ms is classified into the classification "2 ms", each time difference $\Delta t$ satisfying $4 \leq \Delta t < 6$ ms is classified into the classification "4 ms", each time difference $\Delta t$ satisfying $6 \leq \Delta t < 8$ ms is classified into the classification "6 ms", and each time difference $\Delta t$ satisfying $8 \leq \Delta t < 10$ ms is classified into the classification "8 ms".

Figure 8:
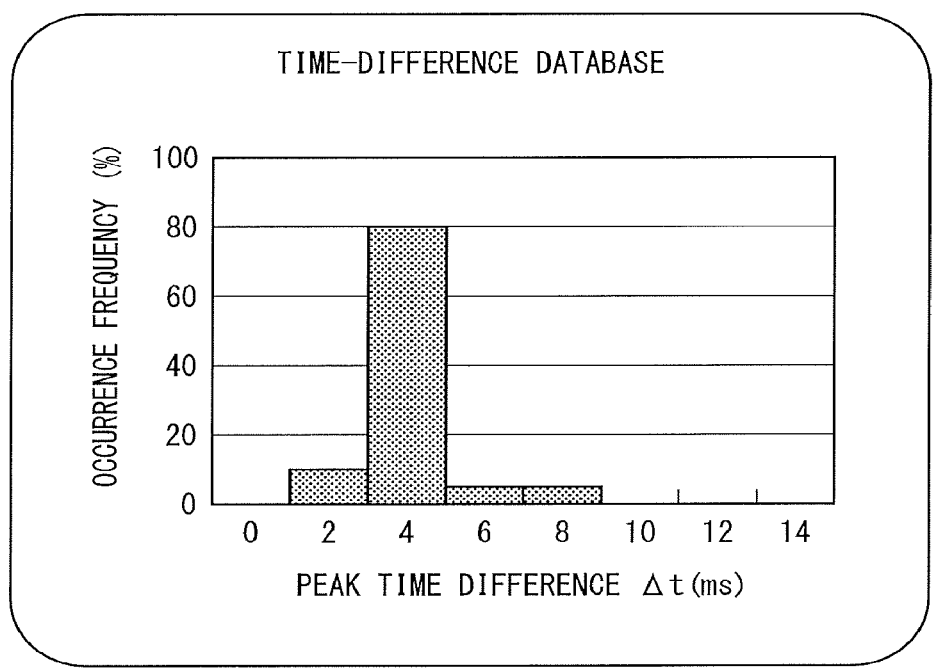
FIG. 8 is the second diagram illustrating the concept of generating and updating the time-difference database.

FIG. 8 is a schematic diagram illustrating the time-difference database 30 constructed as described above in the form of a graph. In FIG. 8, the horizontal axis indicates each classification of the above-described time difference $\Delta t$, and the vertical axis indicates a ratio (%) of the occurrence frequency of the time difference $\Delta t$ to the total number of occurrences. The case shown in FIG. 8 indicates that the occurrence frequency of the time difference $\Delta t$ satisfying $4 \leq \Delta t < 6$ ms (i.e., belonging to the classification "4 ms") is significantly higher than the occurrence frequency of the time difference belonging to any other classification.

Returning to FIG. 5, in the step ST106, the processing circuitry 208 refers to the time-difference database 30 each time the time difference is newly calculated in the step ST105. When it is determined (as YES in the step ST106) that the occurrence frequency classification of the peak time difference in the database 30, corresponding to the calculated peak time difference in the step ST105, is higher than the predetermined threshold value, the processing proceeds to the step ST107.

In the step ST107, since the R-wave is considered to be correctly detected by the determination in step ST 106, the synchronization signal is outputted to the ECG synchronization imaging apparatus 300. After that, the processing proceeds to the step ST108.

Conversely, when it is determined (as NO) in the step ST106 that the occurrence frequency of the peak time difference in the database 30, corresponding to the calculated peak time difference in the step ST105, is lower than the predetermined threshold value, R-wave is considered to be erroneously detected. In this case, the processing proceeds to the step ST108 without outputting the synchronization signal to the ECG synchronization imaging apparatus 300.

In the step ST108, the time-difference database 30 is updated by using the peak time difference Δt calculated in step ST105. In other words, the occurrence frequency of the time difference of the corresponding classification is recalculated by incrementing the total number of peak time differences by one and increasing the number of occurrences of the time difference of the corresponding classification by one. In this manner, the time-difference database 30 is updated.

The step ST109 is determination for stopping. The processing circuitry 208 repeats the processing from the steps ST100 to ST108 until an instruction to terminate the processing is inputted from the outside.

Figure 9:
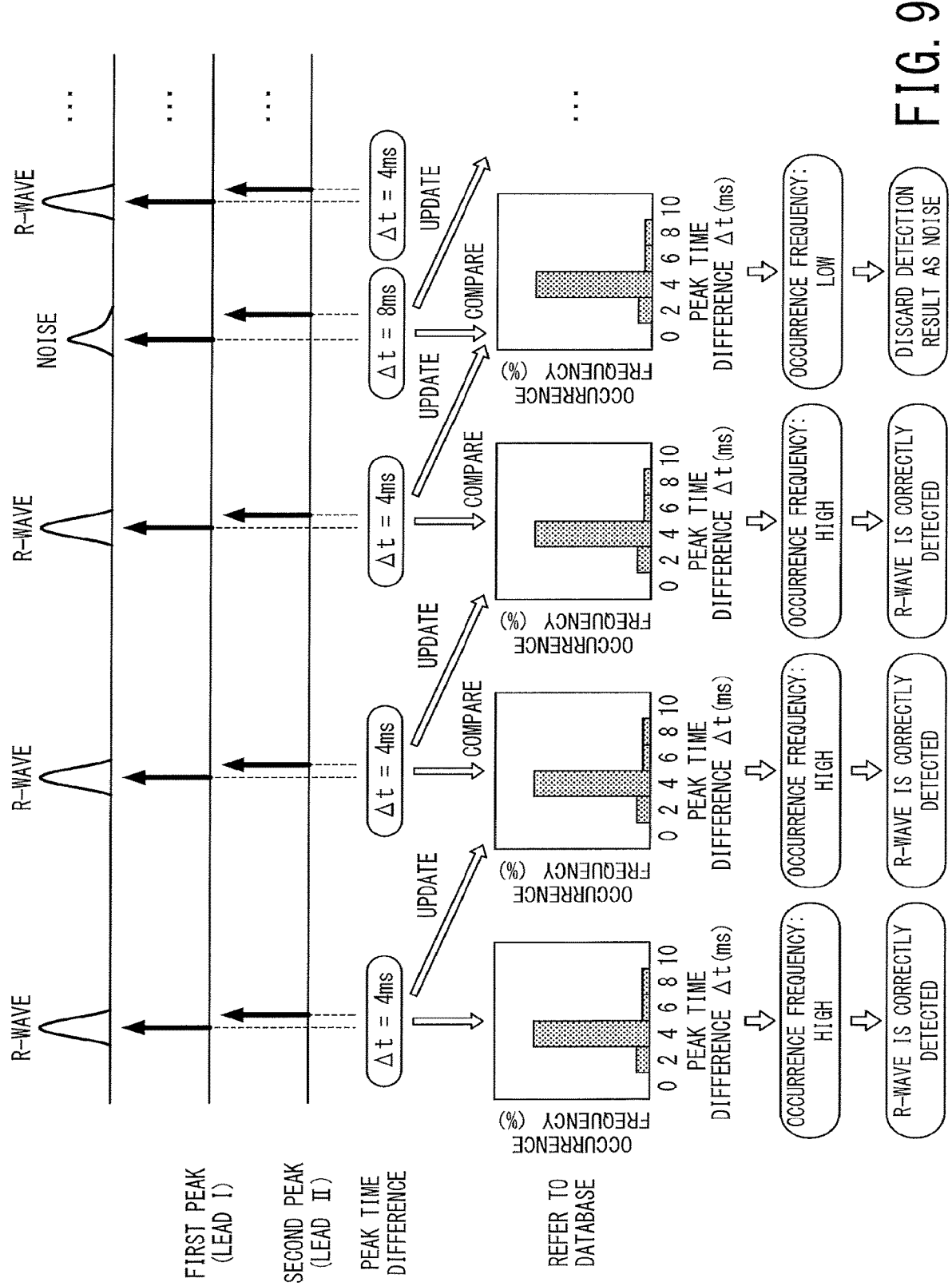
FIG. 9 is a schematic diagram illustrating an outline of an operation performed by the ECG-signal processing apparatus according to the first embodiment.

FIG. 9 is a schematic timing chart illustrating the operation concept from the above-described steps ST100 to ST108. The top part in FIG. 9 is a diagram illustrating an ECG signal including R-waves and noise. The second top part and the third top part in FIG. 9 correspond to the processing from the steps ST100 to ST104. The fourth top part in FIG. 9 corresponds to the processing of the step ST105. The fifth top part and subsequent parts in FIG. 9 correspond to the processing from the steps ST106 to ST108.

As described above, the ECG-signal processing apparatus 1 of the first embodiment uses two peak detection functions including the first-peak detection function 11 and the second-peak detection function 12. The detection accuracy of each of the first-peak and second-peak detection functions 11 and 12 is not necessarily high. However, by comparing the occurrence frequency of the peak time difference between respective peak times detected by both functions 11 and 12 with the corresponding occurrence frequency of the peak time difference accumulated in the time-difference database 30 as the past history, it is possible to reduce the false detection of the noise mixed in the ECG signal as the R-wave.

Figure 10:
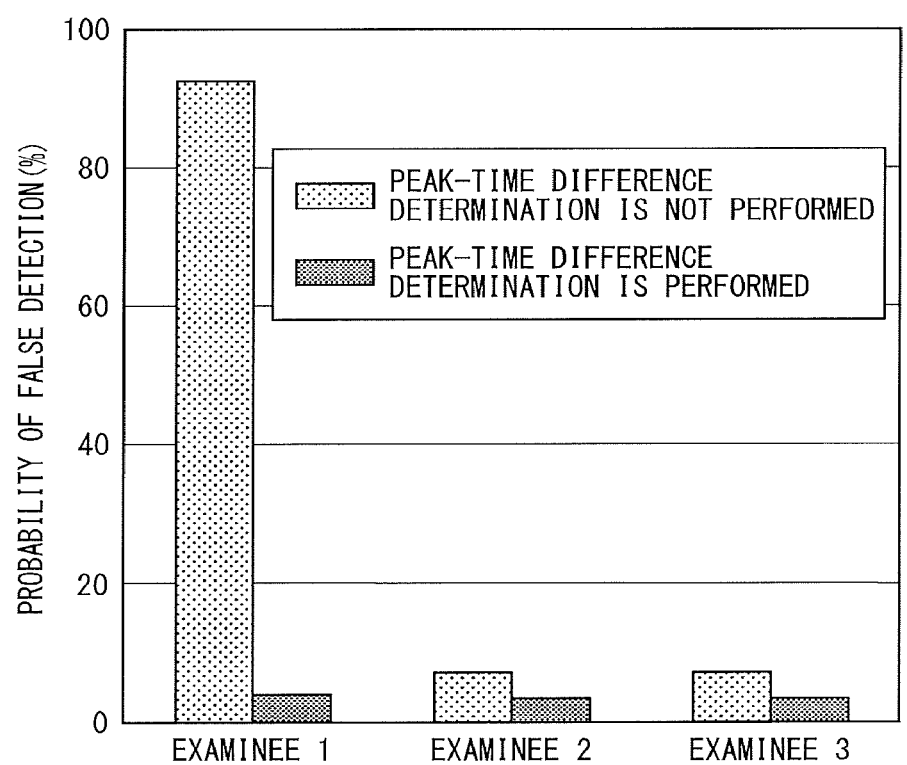
FIG. 10 is a schematic diagram illustrating an evaluation result of R-wave detection.

FIG. 10 is a schematic diagram illustrating a result of performing R-wave detection on ECG signals in order to confirm the effect of the ECG-signal processing apparatus 1 according to the first embodiment. Three volunteers were subjected to MRI examination by using a 3 Tesla MRI apparatus, and then, R-wave detection was performed on the ECG signals acquired during the MRI examination. After that, evaluation was performed based on the number of false detections (i.e., the number of erroneous detections) out of all the R-waves detected by the signal processing apparatus. The horizontal axis of FIG. 10 indicates ID of each examinee. Individual differences are large in the R-wave shape. Regarding the examinee 1, the probability of false detection was very high when only the conventional peak detection was performed. Meanwhile, regarding the examinees 2 and 3, the probability of false detection was not so high even when only the conventional peak detection was performed.

By contrast, when the determination with the use of the peak time difference of the above-described embodiment was performed, the probability of the false detection was greatly improved for the examinee 1. In addition, even in the cases of the examinees 2 and 3, the probability of the false detection was reduced. In this way, in any case, it is possible to reduce the probability of the false detection by performing the determination with the use of the peak time difference of the present embodiment, and the effect of the above-described processing of the ECG-signal processing apparatus 1 was confirmed.

Modification of the First Embodiment

Figure 11:
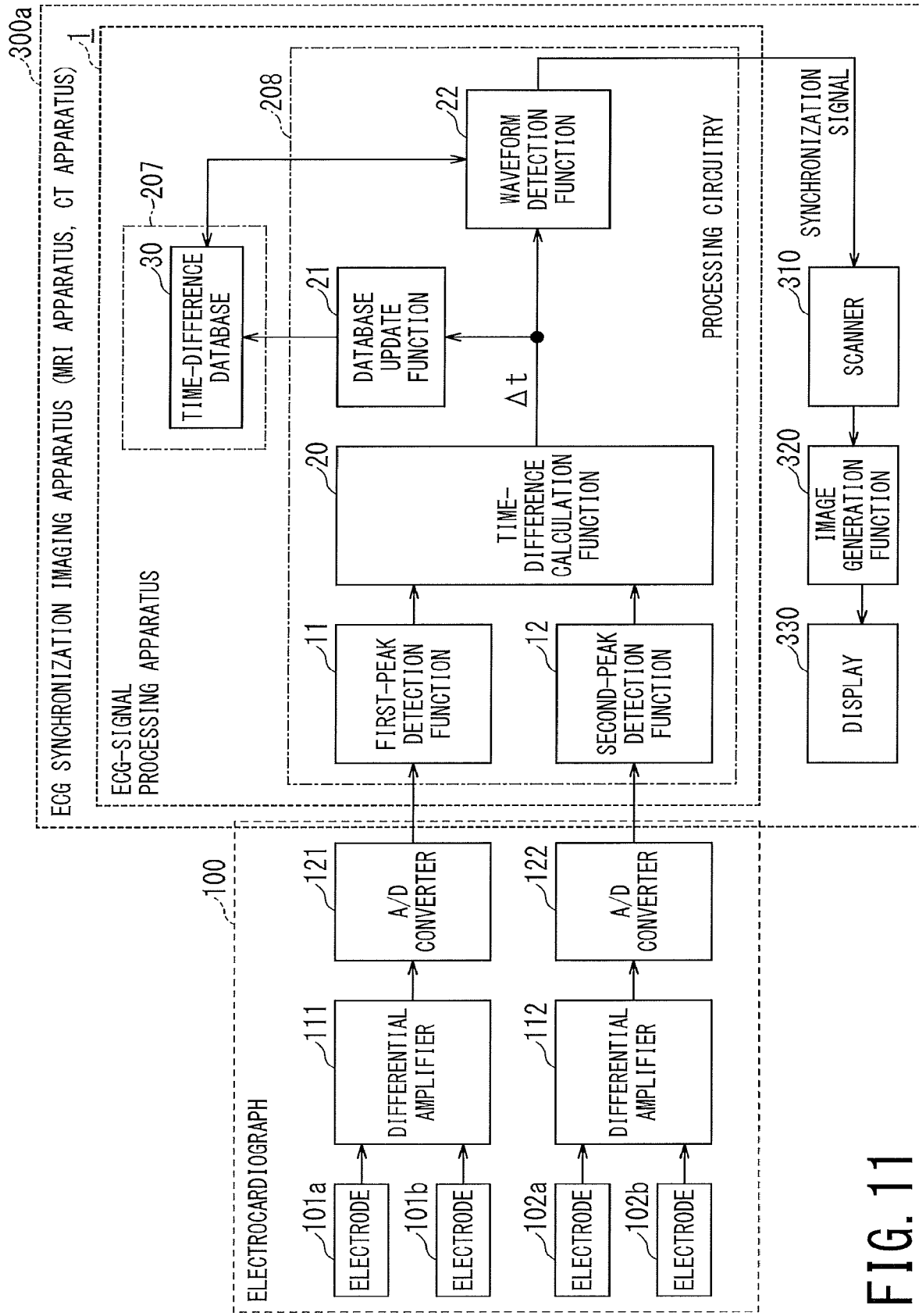
FIG. 11 is a block diagram illustrating a configuration of a modification of the first embodiment.

FIG. 11 is a block diagram illustrating a configuration of a modification of the first embodiment. In the modification of the first embodiment, the ECG-signal processing apparatus 1 is included in an ECG synchronization imaging apparatus 300a.

In FIG. 11, a scanner 310 is an apparatus that performs imaging in synchronization with the synchronization signal outputted from the ECG-signal processing apparatus 1.

For instance, when the ECG synchronization imaging apparatus 300a is an MRI apparatus, the scanner 310 includes components such as a static magnetic field magnet, a gradient coil, an RF coil, a transmitter, and a receiver. The scanner 310 performs ECG synchronization imaging in synchronization with the synchronization signal detected from the R-wave so as to acquire MR signals of an object. An image generation function 320 of processing circuitry of the MRI apparatus reconstructs an image by using the acquired MR signals.

Alternatively, when the ECG synchronization imaging apparatus 300a is a CT apparatus, for instance, the scanner 310 includes components such as an X-ray tube, an X-ray detector, and a DAS (Data Acquisition System). Also in this case, the scanner 310 performs ECG synchronization imaging in synchronization with the synchronization signal detected from the R-wave so as to acquire projection data for an object. The image generation function 320 of the processing circuitry of the CT apparatus reconstructs an image by using the acquired projection data.

The image generated by the image generation function 320 of the MRI apparatus or the CT apparatus is displayed on a display 330. The display 330 may display the ECG signal acquired from the electrocardiograph 100 and/or the synchronization signal acquired from the signal processing apparatus 1.

Second Embodiment

Figure 12:
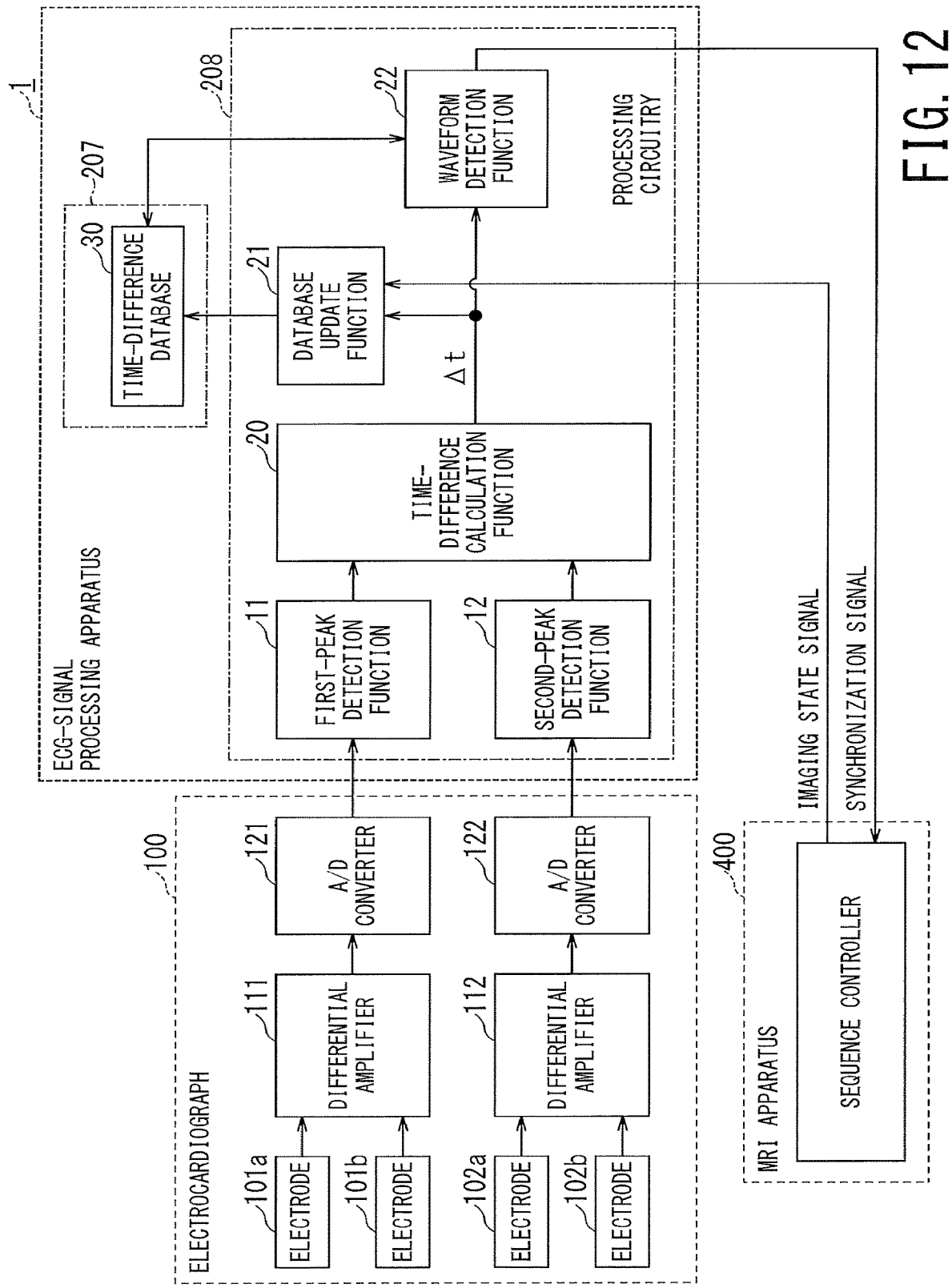
FIG. 12 is a block diagram illustrating a configuration of the ECG-signal processing apparatus according to the second embodiment.

FIG. 12 is a block diagram illustrating a configuration of the ECG-signal processing apparatus 1 of the second embodiment and a configuration of apparatuses connected to the ECG-signal processing apparatus 1.

As compared with the configuration of the ECG-signal processing apparatus 1 of the first embodiment shown in FIG. 4, the second embodiment differs from the first embodiment in that the ECG synchronization imaging apparatus 300 in FIG. 4 is replaced by the MRI apparatus 400 and "an imaging state signal" is outputted from a sequence controller of the MRI apparatus 400 to the database update function 21 of the ECG-signal processing apparatus 1. Excluding these two points, the ECG-signal processing apparatus 1 of the second embodiment has the same configuration as the ECG-signal processing apparatus 1 of the first embodiment.

In general, since a gradient magnetic field and a high-frequency magnetic field are applied in a period during which imaging is performed by the MRI apparatus 400, there is a high possibility that large noise is mixed in ECG signals. Thus, when the time-difference database 30 is generated or updated in a period during which imaging is performed by the MRI apparatus 400, there is a high possibility that quality of the database to be generated or updated is deteriorated by being affected by noise.

For this reason, in the second embodiment, the MRI apparatus 400 is configured to monitor "an operation state". Then, when the operation state of the MRI apparatus 400 is "in the imaging state" or "in operation", generation or update of the time-difference database 30 is prohibited and the MRI apparatus 400 performs generation or update of the time-difference database 30 only when the MRI apparatus 400 is "in the non-imaging state" or "not in operation".

In order to determine whether the MRI apparatus 400 is "in the imaging state (i.e., in operation)" or "in the non-imaging state", the imaging state signal outputted from the MRI apparatus 400 is used.

In the MRI apparatus 400, data are acquired by executing a pulse sequence in which imaging conditions such as intensity and application timing of each gradient pulse and each RF pulse are defined. Additionally, a unit of imaging from the start of executing a pulse sequence until completion of acquiring predetermined data by repeating the necessary number of TR (Repetition Time) is called, e.g., "protocol". In the present specification, when the MRI apparatus 400 is "in the imaging state" or "in operation", this means it is in a period during which a pulse sequence is executed, for instance. Conversely, in the present specification, when the MRI apparatus 400 is "in the non-imaging state" or "not in operation", this means, e.g., it is in a period during which a pulse sequence is not executed. For instance, a period before starting the first protocol included in a series of examinations or a period between a protocol and the next protocol may correspond to "in the non-imaging state" and "not in operation". Further, in a period of one TR included in the pulse sequence, there may be a period during which neither gradient pulse nor RF pulse is applied, and such a period can also be treated as "in the non-imaging state" or "not in operation".

A signal indicating whether a gradient pulse and/or an RF pulse is applied or not can be used as the imaging state signal for determining whether the MRI apparatus 400 is "in the imaging state (i.e., in operation)".

Figure 13:
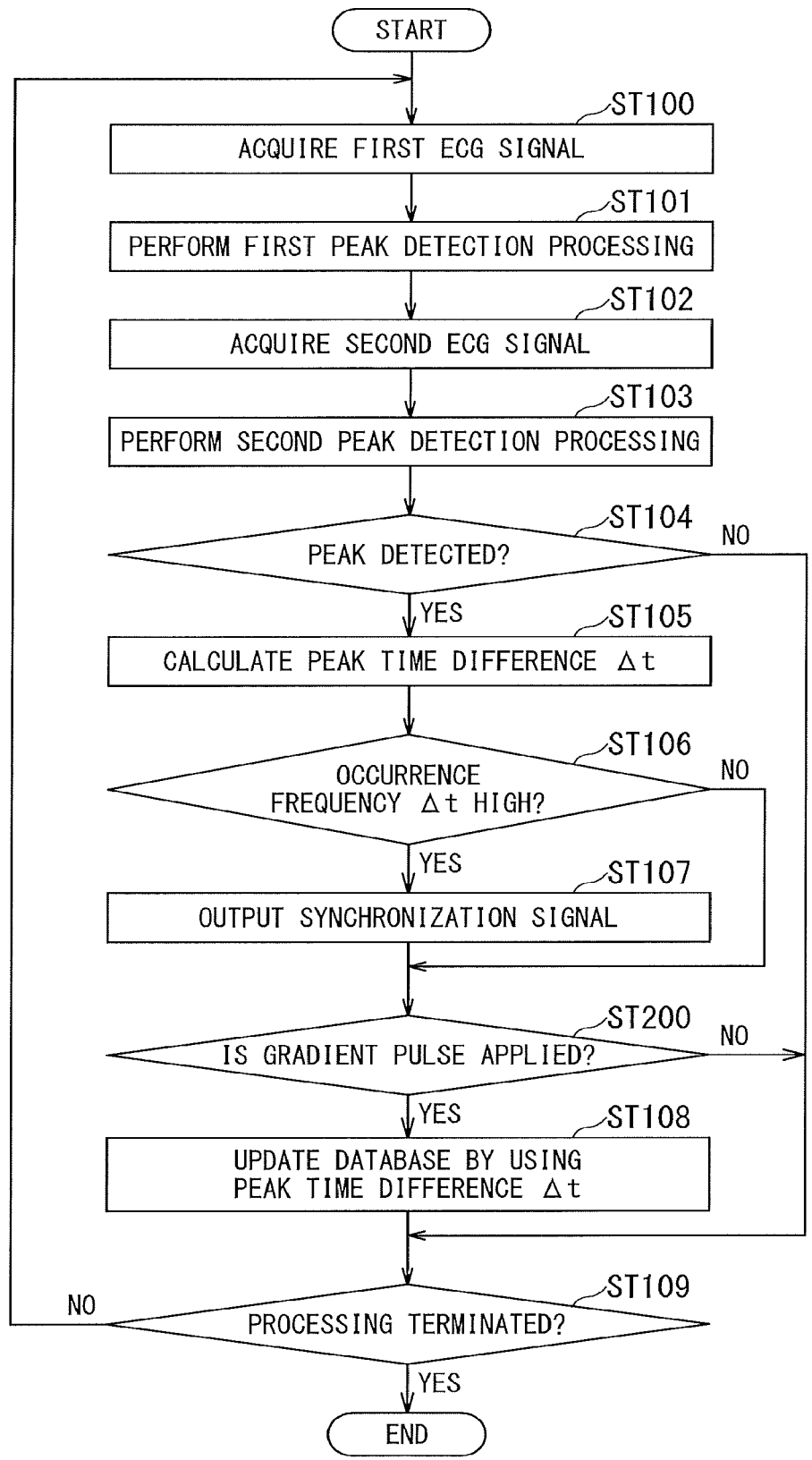
FIG. 13 is a flowchart illustrating processing performed by the ECG-signal processing apparatus according to the second embodiment.

FIG. 13 is a flowchart illustrating an operation performed by the ECG-signal processing apparatus 1 according to the second embodiment, which differs from the first embodiment (FIG. 5) only in that the processing of the step ST200 is added between the steps ST107 and ST108.

In the step ST200, on the basis of the imaging state signal, it is determined whether a gradient pulse is applied or not. Only when the gradient pulse is not applied (i.e., only when it is in the non-imaging state and determined as NO in the step ST200), the processing proceeds to the next step ST108 in which the time-difference database 30 is updated.

The ECG-signal processing apparatus 1 of the second embodiment stops update of the time-difference database 30 the non-imaging state, during which noises due to switching of a gradient pulse are mixed in the ECG signal, and thus, peak detection becomes difficult. Accordingly, the ECG-signal processing apparatus 1 of the second embodiment can prevent erroneously updating the time-difference database 30 due to the noises.

In the ECG-signal processing apparatus 1 according to the second embodiment as described above, since the time-difference database 30 can be generated with high-quality without being influenced by noise, it is possible to accurately detect the R-wave.

According to the ECG signal processing apparatus according to at least one embodiment described above, it is possible to accurately detect a specific waveform from a biological signal related to heartbeat in which noise is mixed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A signal processing apparatus configured to be connected to an imaging apparatus and an electrocardiograph including at least two leads, the leads being configured to receive a plurality of biological signals related to a heartbeat of a patient, the signal processing apparatus comprising:
  a memory configured to store a predetermined program and a time-difference database in which difference in peak time and occurrence frequency of the difference in peak time are associated with each other; and
  processing circuitry configured, by executing the predetermined program, to:
    detect respective peaks of the plurality of biological signals received from the electrocardiograph,
    calculate difference in peak time between the plurality of biological signals,
    update the time-difference database each time a peak of the plurality of biological signals is detected and the difference in peak time between the plurality of biological signals is calculated,
    refer to the time-difference database, and
    detect a specific waveform included in the plurality of biological signals when an occurrence frequency in the time-difference database associated with difference in peak time between respective peaks of the plurality of newly detected biological signals is higher than a predetermined occurrence frequency.

2. The signal processing apparatus according to claim 1, wherein the plurality of biological signals are ECG signals; and
  the specific waveform is an R-wave.

3. The signal processing apparatus according to claim 1, wherein the plurality of biological signals are received from a lead I and a lead II included in ECG signals; and
  the processing circuitry is further configured to detect the specific waveform based on difference in peak time between a first peak detected from a signal of the lead I and a second peak detected from a signal of the lead II.

4. The signal processing apparatus according to claim 1, wherein the processing circuitry is further configured to:
monitor an operation state of the imaging apparatus, and
determine whether to update the time-difference database or not, according to the operation state of the imaging apparatus.

5. The signal processing apparatus according to claim 4, wherein the imaging apparatus is an MRI apparatus; and the processing circuitry is further configured to:
update the time-difference database based on time difference of a peak detected in a period during which the MRI apparatus does not perform imaging, and
hold the time-difference database in a period during which the MRI apparatus perform imaging, without updating the time-difference database.

6. An imaging apparatus configured to be connected to an electrocardiograph including at least two leads, the leads being configured to receive a plurality of biological signals related to a heartbeat of a patient, the imaging apparatus comprising:
a memory configured to store a predetermined program and a time-difference database in which difference in peak time and occurrence frequency of the difference in peak time are associated with each other;
processing circuitry configured, by executing the predetermined program, to:
detect respective peaks of the plurality of biological signals received from the electrocardiograph,
calculate difference in peak time between the plurality of biological signals,
update the time-difference database each time a peak of the plurality of biological signals is detected and the difference in peak time between the plurality of biological signals is calculated,
refer to the time-difference database,
detect a specific waveform included in the plurality of biological signals when an occurrence frequency in the time-difference database associated with difference in peak time between respective peaks of the plurality of newly detected biological signals is higher than a predetermined occurrence frequency, and
generate a synchronization signal from the detected specific waveform; and
a scanner configured to:
receive the synchronization signal, and
acquire imaging data of an object by imaging the object in synchronization with the received the synchronization signal and generate an image of the object based on the imaging data.

7. A signal processing method comprising:
detecting respective peaks of a plurality of biological signals, the plurality of biological signals being related to a heartbeat of a patient and received from a plurality of leads included in an electrocardiograph;
calculating difference in peak time between the plurality of biological signals;
updating a time-difference database, in which difference in peak time and occurrence frequency of the difference in peak time are associated with each other, each time a peak of the plurality of biological signals is detected and the difference in peak time between the plurality of biological signals is calculated;
referring to the time-difference database; and
detecting a specific waveform included in the plurality of biological signals when an occurrence frequency in the time-difference database associated with difference in peak time between respective peaks of the plurality of newly detected biological signals is higher than a predetermined occurrence frequency.

* * * * *